United States Patent [19]

Doyle et al.

[11] 4,032,544
[45] June 28, 1977

[54] 3-CYANO-4-HYDROXY COUMARIN DERIVATIVES

[75] Inventors: Frank Peter Doyle, Leatherhead; Barrie Christian Charles Cantello, Horsham; Derek Richard Buckle, Redhill; Harry Smith, Maplehurst, all of England

[73] Assignee: Beecham Group Limited, England

[22] Filed: June 28, 1976

[21] Appl. No.: 700,512

Related U.S. Application Data

[62] Division of Ser. No. 572,226, April 28, 1975, Pat. No. 4,012,407.

[30] Foreign Application Priority Data

May 4, 1974 United Kingdom ............ 19721/74

[52] U.S. Cl. ..................... 260/343.2 R; 260/465 F; 424/281; 424/304
[51] Int. Cl.² ..................................... C07D 311/06
[58] Field of Search ................................ 260/343.2

[56] References Cited

UNITED STATES PATENTS 3,521,187   7/1970   Snavely et al. ............ 260/343.2 R

OTHER PUBLICATIONS

Cecchi et al. *Chemical Abstracts* 65, 16931h, 1966.

*Primary Examiner*—Lorraine A. Weinberger
*Assistant Examiner*—Jane T. Fan

[57] ABSTRACT

Compounds of the formula

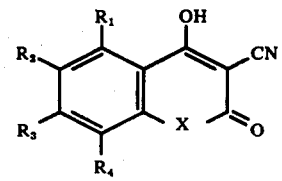

and pharmaceutically acceptable, nontoxic salts thereof or hydrates thereof, wherein $R_1$, $R_2$, $R_3$ and $R_4$ are each hydrogen, halogen, lower alkyl or lower alkoxy, or any two of the groups $R_1$, $R_2$, $R_3$ and $R_4$, taken together with the carbon atoms to which they are joined complete a substituted or unsubstituted carbocyclic ring, and X is an oxygen atom, provided that $R_1$, $R_2$, $R_3$ and $R_4$ are not all simultaneously hydrogen, are useful for treating allergic conditions in humans.

The compounds may be prepared by reacting a suitably substituted benzene derivative with an activated carbonyl group having a carbanion of the formula NC-CH-R, wherein R is a carboxylic acid ester group, and thereafter, if desired, converting the compound into a salt.

17 Claims, No Drawings

3-CYANO-4-HYDROXY COUMARIN DERIVATIVES

This is a division of application Ser. No. 572,226, filed Apr. 28, 1975, now U.S. Pat. No. 4,012,407.

This invention relates to pharmaceutical compositions and novel compounds which are useful in the inhibition of the effects of certain types of antigen-antibody reactions, and are therefore of value in the prophylaxis and treatment of diseases associated with allergic or immunological reactions, e.g. certain types of asthma and hay-fever and also in the treatment of rhinitis. The invention also includes methods for the preparation of these novel compounds.

We have discovered that compounds of the formula (I):

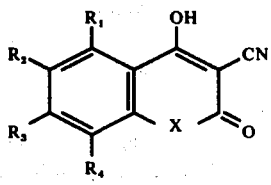

and pharmaceutically acceptable salts thereof, wherein $R_1$, $R_2$, $R_3$ and $R_4$ are each a hydrogen or halogen atom, or an alkyl, or alkoxy group or any two of the groups $R_1$, $R_2$, $R_3$ and $R_4$ taken together with the carbon atoms to which they are joined complete a substituted or unsubstituted carbocylic ring, and X represents a bond, or an oxygen atom, have useful activity in mammals in that they inhibit the effects of certain types of antigen-antibody reactions. However a literature search has revealed that not all of the compounds of formula (I) are novel.

Below we list the two compounds of the formula (I) which we have found mentioned in the literature, together with the appropriate literature reference:

2-Cyanoindan-1,3-dione[1]
3-Cyano-4-hydroxycoumarin[2]
References
1. Zh. Org. Khim, 9, 1307 (1973).
2. Gazz. Chim. Ital (1968), 98, 1488 (Chem. Abs., 70, 96547).

Although the above compounds have been reported in the literature no form of useful biological activity has been ascribed to them. Likewise there has been in the literature no suggestion that such compounds are likely to possess any form of useful biological activity and in particular the discovery that they have anti-allergic activity has not been predicted in any way.

Accordingly, in its broadest aspect, the present invention provides a pharmaceutical composition having anti-allergy activity comprising a compound of the formula

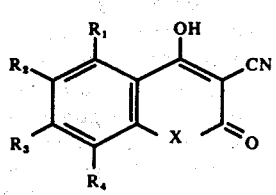

or a pharmaceutically acceptable salt thereof, wherein $R_1$, $R_2$, $R_3$ and $R_4$ are each a hydrogen or halogen atom, or an alkyl, or alkoxy group, or any two of the groups $R_1$, $R_2$, $R_3$ and $R_4$ taken together with the carbon atoms to which they are joined complete a substituted or unsubstituted carbocylic ring, and X represents a bond, or an oxygen atom, together with one or more pharmaceutically acceptable carriers.

Suitably the alkyl and alkoxy groups have from 1 to 6 carbon atoms, preferably 1 to 3 carbon atoms. Examples of the groups $R_1$, $R_2$, $R_3$ and $R_4$ which may be present in compounds of the formula (I) include hydrogen, fluorine, chlorine, bromine and iodine atoms, and methyl, ethyl, n- and iso-propyl, n-, sec- and tert-butyl, methoxy, ethoxy, n- and iso-propoxy, n-, sec- and tert-butoxy. In addition the groups $R_1$ and $R_2$, $R_2$ and $R_3$ or $R_3$ $R_4$ taken together with the carbon atoms to which they are joined may form a fused phenyl, 1,2-cyclopentylene or 1,2-cyclohexenylene ring which may carry one or more of the substitutents listed above.

Preferably the groups $R_1$ and $R_4$ are each hydrogen atoms, and one or both of the groups $R_2$ and $R_3$ are methyl, ethyl, n-propyl, methoxy, ethoxy or n-propoxy groups.

Examples of suitable salts of compounds of the formula (I) include the alkali metal salts, particularly potassium and sodium, and the alkaline earth metal salts, such as aluminum and magnesium salts, as well as salts with organic bases such as amines or amino compounds.

Suitable compounds which may be incorporated into the compositions of this invention include the following:

2-cyano indan-1,3-dione;
2-cyano-5-methyl indan-1,3-dione;
2-cyano-5,6-dimethyl indan-1,3-dione;
2-cyano-4-methyl indan-1,3-dione;
2-cyano-4-methoxy indan-1,3-dione;
5,6-benzo-2-cyano indan-1,3-dione;
5-chloro-2-cyano indan-1,3-dione;
2-cyano-5,6-diethyl indan-1,3-dione;
3-cyano-4-hydroxycoumarin;
3-cyano-6-ethyl-4-hydroxy-7-methyl coumarin;
3-cyano-6,7-dimethyl-4-hydroxycoumarin monohydrate;
3-cyano-6,7-diethyl-4-hydroxycoumarin;
3-cyano-4-hydroxy-6-methyl coumarin;
3-cyano-4-hydroxy-7-methyl coumarin;
3-cyano-7-ethyl-4-hydroxy coumarin;
3-cyano-7-ethoxy-4-hydroxy coumarin monohydrate;
3-cyano-4-hydroxy-2-oxo-2H-naphtho[2,3-b]pyran;
3-cyano-4-hydroxy-2-oxo-6,7,8,9-tetrahydro-2H-naphtho[2,3-b]pyran;
3-cyano-4-hydroxy-8-methylcoumarin monohydrate;
3-cyano-4-hydroxy-6-methyloxycoumarin;
3-cyano-7,8-dimethyl-3-hydroxycoumarin monohydrate.

The compounds of formula (I) may exist in a number of tautomeric forms, and it is to be understood that whenever in the specification we refer to compounds of the formula (I) we mean to include tautomeric forms thereof. The tautomeric forms predominant for a particular compound of formula (I) are dependent on the nature of the substituent X. When X represents a bond, the predominant tautomers include:

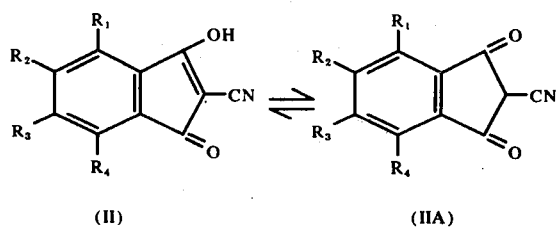

(II)                                    (IIA)

When X represents an oxygen atom, the predominant tautomers include:

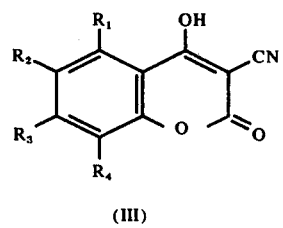

(III)

The compositions of this invention are adapted for administration to human being and may be presented as a microfine powder for insufflation, e.g. as a snuff or in capsules of hard gelatin. In such a case the particles of active compound suitably have diameters less than 50 microns, preferably less than 10 microns. Compositions may be presented with a sterile liquid carrier for injection. Compounds of formula (I) which are active when given by the oral route, may be compounded in the form of syrups, tablets, capsules, pills and the like. Preferably the compositions are in unit dosage form, or in a form in which the patient can administer to himself a single dosage. For example when the composition is in the form of a tablet, pill or capsule, a suitable dosage unit might contain from 1 to 500 mg. of active ingredient. If desired, a small amount of bronchodilator compound such as isoprenaline may be incorporated into the compositions of this invention both to inhibit the cough response if the composition is insufflated and to provide immediate relief during an asthmatic attack. The effective dose of compound (I) depends on the particular compound employed, but is in general in the range of from 0.1 mg/kg/day to 100 mg/kg/day.

The precise nature of the pharmaceutical carrier used in the compositions of this invention is not important. Standard pharmaceutical practice may be followed.

As in common practice, the compositions will usually be accompanied by written or printed directions for use in the medical treatment concerned, in this case as an anti-allergic agent for prophylaxis or treatment of, for example, asthma, hay-fever or rhinitis.

In a second aspect, this invention provides novel compounds of the formula (I):

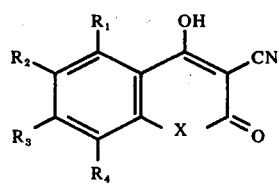

and pharmaceutically acceptable salts thereof, wherein $R_1$, $R_2$, $R_3$ and $R_4$ are each a hydrogen or halogen atom, or an alkyl, or alkoxy group or any two of the groups $R_1$, $R_2$, $R_3$ and $R_4$ taken together with the carbon atoms to which they are joined complete a substituted, or unsubstituted carbocyclic ring, and X represents a bond, or an oxygen atom; provided that the groups $R_1$, $R_2$, $R_3$ and $R_4$ are not all hydrogen atoms.

The identities and the preferred values of the groups $R_1$, $R_2$, $R_3$ and $R_4$ have already been discussed in relation to the pharmaceutical compositions of the invention, and the same remarks apply here.

The method of preparation of the novel compounds of this invention depends on the value of the substituent X in formula (I).

When X represents a bond, the novel compounds are of the formula (II):

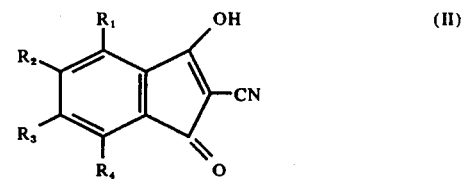

and pharmaceutically acceptable salts thereof, wherein $R_1$, $R_2$, $R_3$ and $R_4$ are as defined with reference to the formula (I), except that $R_1$, $R_2$, $R_3$ and $R_4$ may not all be hydrogen atoms. These compounds may be prepared by reacting an appropriately substituted 3-cyanomethylene phthalide of the formula (V):

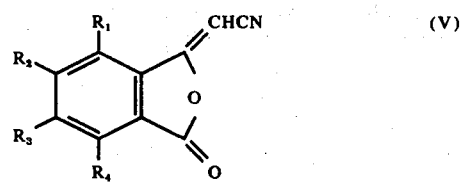

wherein $R_1$, $R_2$, $R_3$ and $R_4$ are as defined with reference to formula (II), with a base, and thereafter if desired converting the thus formed compound of the formula (II) to a salt thereof.

We have found the most suitable bases for this reaction to be those of the formula $MOR^1$, wherein M is an alkali metal or alkaline earth metal ion and $R^1$ is the organic residue of a straight chain alcohol containing one to four carbon atoms. Examples of such bases include sodium methoxide and sodium ethoxide. However, other bases may be used, including tertiary bases such as pyridine, picoline and trialkylamines such as triethylamine.

The choice of solvent for this reaction depends on the base used. For example when the base is an alkoxide as defined above then a suitable solvent is the corresponding alcohol. Similarly, when the base used is a tertiary base, then that base may itself be the solvent for the reaction, or alternatively an inert solvent such as a diloweralkyl ether, dioxan, tetrahydrofuran or dimethylsulphoxide may be used.

The known compound 2-cyanoindan-1,3-dione (formula (II) wherein $R_1$, $R_2$, $R_3$ and $R_4$ are all hydrogen atoms) may also be prepared by this process, using the corresponding unsubstituted intermediates.

The compounds of formula (V) may in turn be prepared by treating a suitably substituted phthalic anhydride with cyanoacetic acid in the presence of a base, such as pyridine, as activator. It is to be noted that when the anhydride is asymmetrically substituted in the phenyl ring, then this reaction yields isomeric cyanomethylene phthalides of the formula (V). However these isomers yield only one compound of the formula (II) on base treatment.

The intermediates of formula (V) may also be prepared by the route shown in scheme I (see H. W. Moore, Chem. Soc. Reviews, 2, 41.5 (1973)).

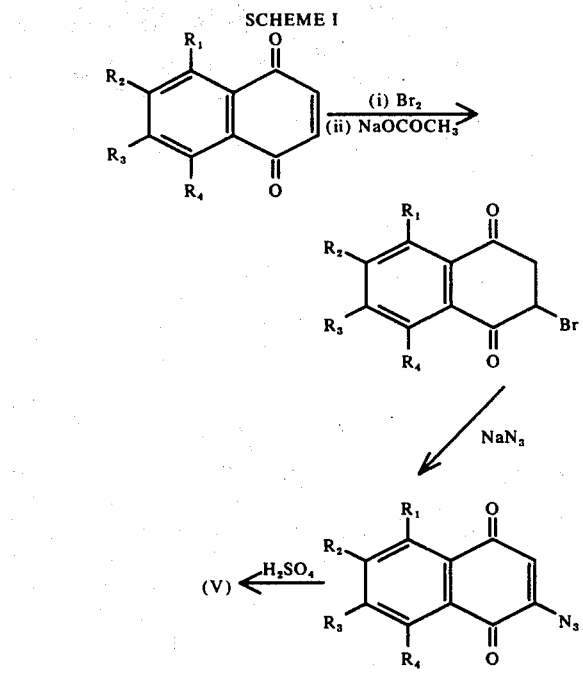

An alternative method of preparation of compounds of formula (II) when X represents a bond in the reaction of a compound of formula (IX):

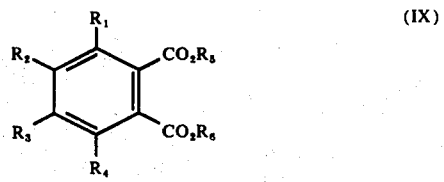

wherein $R_1$, $R_2$, $R_3$, and $R_4$ are as defined with reference to formula (I) and $R_5$ and $R_6$ are the same or different and each is an alkyl group; with acetonitrile in the presence of a base, and thereafter if desired converting the thus formed compound of formula (II) to a salt thereof.

Suitable bases for this reaction are strong bases such as alkali metal or alkaline earth metal salts of aliphatic alcohols, especially those containing from 1 to 4 carbon atoms, for example sodium methoxide and sodium ethoxide.

When X represents an oxygen atom, the novel compounds are of the formula (III):

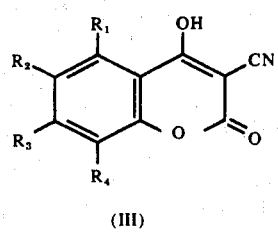

and pharmaceutically acceptable salts thereof, wherein $R_1$, $R_2$, $R_3$ and $R_4$ are as defined with reference to formula (I), except that $R_1$, $R_2$, $R_3$ and $R_4$ may not be all hydrogen atoms. These compounds may be prepared by reacting a suitably substituted benzene derivative of the formula (VI):

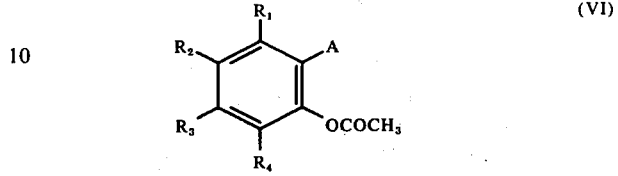

wherein $R_1$, $R_2$, $R_3$ and $R_4$ are as defined with reference to formula (II) and A represents an activated carbonyl group, which a carbanion of the formula NC—CH—R, wherein R represents a carboxylic ester group, and thereafter if desired converting the thus formed compound of the formula (III) to a salt thereof.

The carbanion NC—CH—R may be prepared by the reaction of the compound NC—CH$_2$—R$^2$ with a base. Suitable bases for this proton abstraction include sodium ethoxide and sodium hydride.

The group A represents an activated carbonyl derivative, and such groups include groups of the formula —CO.B. wherein B is a chlorine or bromine atom, or the residue of a mixed anhydride. B preferably represents a chlorine atom.

The nature of the carboxylic ester group R is not critical to the success of the reaction, but we have found that alkyl esters wherein the alkyl moiety contains one to four carbon atoms, such as the ethyl ester, are particularly suitable.

The reaction is preferably carried out in an inert, anhydrous solvent. Suitable solvent include diloweralkylethers such as diethylether; dioxan, tetrahydrofuran and dimethylsulphoxide.

The known compound 3-cyano-4-hydroxycoumarin (formula (III) wherein $R_1$, $R_2$, $R_3$ and $R_4$ are all hydrogen atoms) may also be prepared by this process. In this case an unsubstituted compound of the formula (VI) is used as the starting material.

The following Examples illustrate the preparation and properties of a number of compounds of formula (I).

EXAMPLE 1 a. 3-Cyanomethylene phthalide

A finely powdered mixture of phthalic anhydride (34 g.; 0.23 mole) and cyanoacetic acid (22 g.; 0.26 mole) was dissolved in dry pyridine (28 ml) and the mixture stirred for 6 hours at 60°–70° C. After cooling overnight the dark solid was treated with water (800 ml) and brought the pH 4–5 with hydrochloric acid. The resulting yellow solid was filtered off, washed well with water and recrystallised from glacial acetic acid, m.p. 178°–180° C (lit. m.p. 195° C).

b. 2-Cyano indan-1,3-dione

3-Cyanomethylene phthalide (6.0 g.; 0.035 mole) was added to a solution of sodium (0.8 g.) in methanol (35 ml) and the red solution refluxed for 20 mins. On cooling and acidification with one-third of its bulk of concentrated hydrochloric acid the indandione separated as a copious yellow solid, m.p. 204°–207° C (d) (lit. m.p. 201°–202° C).

EXAMPLE 2 a. 3-Cyanomethylene-5 or 6-methyl phthalide

Powdered 4-methyl phthalic anhydride (37.2 g.; 0.23 mole) and cyanoacetic acid (22g. 0.26 mole) were dissolved in dry pyridine (28 ml) and the mixture stirred at 60°–70° C for 6 hours.

After fooling and pouring into water (800 ml) the mass was brought to pH 3 with concentrated hydrochloric acid. The oily phthalide was filtered off and recrystallised from glacial acetic acid as a buff solid, m.p. 151°–152° C. (Found C, 71.19; H, 4.08; N, 7.49; $C_{11}H_7NO_2$ requires C, 71.35; H, 3.81; N, 7.56%).

b. 2-Cyano-5-methyl indan-1,3-dione

To a solution of sodium (0.62 g.) in methanol (27 ml.) was added the mixture of 5 and 6 methyl cyanomethylene phthalides from example 2a (5.0 g; 0.027 mole). After refluxing the resulting red solution for 20 mins. it was cooled and treated with one-third of its bulk of concentrated hydrochloric acid. The precipitated yellow dione was filtered off and recrystallised from water; hydrochloric acid, m.p. 176°–178° C. (Found; C, 60.50; H, 4.20; N, 6.39; $C_{11}H_7NO_2.2H_2O$ requires; C, 59.73; H, 5.01; N, 6.33%).

EXAMPLE 3 a. 2-Bromo-6,7-dimethyl naphtho-1,4-quinone

A solution of 6,7-dimethyl naphtho-1,4-quinone (20.0 g.; 0.107 mole) in glacial acetic acid (250 ml) was stirred during the dropwise addition of bromine (5.6 ml; 17.2 g; 0.107 mole) in acetic acid (10 ml.) at 15° C and allowed to stir at this temperature for a further 2 hours. Anhydrous sodium acetate (20 g) was added and the mixture stirred at 100° C for 1½ hours after an initial half hour period at room temperature; cooled, poured into water (2.5 l) and the yellow bromo product filtered off. It had m.p. (ethanol, chloroform) 156°–159° C. (Found; C, 53.47; H, 3.39; Br, 30.23; $C_{12}H_9BrO_2$ requires; C, 54.36; H, 3.42; Br, 30.14%):

b. 2-Azido-6,7-dimethyl napto-1,4-quinone

An aqueous solution of sodium azide (4.4 g; 0.068 mole) was added at once to a refluxing suspension of 2-bromo-6,7-dimethyl naphtho-1,4-quinone (13.8 g; 0.052 mole) in ethanol (130 ml) and the resulting red solution refluxed for a further 2 mins. After cooling in ice the precipitated azide was separated, washed well with water and recrystallised from ethanol as an orange-red solid, m.p. 116°–119° C (d).

c. 3-Cyanomethylene-5,6-dimethyl phthalide

2-Azido-6,7-dimethyl napto-1,4-quinone (2.0 g) was added in small portions (10 mg) to cold (0°–5° C), vigorously stirred concentrated sulphuric acid (30 ml. over 1½ hours and the red solution stirred a further 10 minutes at 3° C until nitrogen evolution ceased. Poured onto ice-water (400 g) whereby the phthalide separated as a whitish solid. After recrystallisation from ethanol in the presence of charcoal the white solid had m.p. 165°–181° C (mixture of E and Z isomers). (Found; C, 72.10; H, 4.77; N, 6.91; $C_{12}H_9NO_2$ requires; C, 72.35; H, 4.55; N, 7.03%).

d. 2-Cyano-5,6-dimethyl indan-1,3-dione

A solution of 3-cyanomethylene-5,6-dimethyl phthalide (2.0 g) and sodium (0.23 g) in methanol (10 ml) was refluxed for 20 mins. cooled and acidified with 5 N hydrochloric acid (50 ml). Extraction of the precipitated solid with 3 × 3000 ml of hot water followed by acidification of the extracts with 300 ml of concentrated hydrochloric acid gave the cyano indandione as a yellow-orange solid, m.p. 209°–210° C (d). (Found; C, 69.61; H, 5.14; N, 6.71; $C_{12}H_9NO_2.$ ½$H_2O$ requires; C, 69.22; H, 4.84; N, 6.72%.)

EXAMPLE 4 a. 3-Cyanomethylene 4 and 7-methyl phthalide

By a similar procedure to that outlined in Example 3, 2-Azido-5-methyl naphtho-1,4-quinone (6.4 g) was ring contracted to a mixture of the 4- and 7-methyl 3-cyanomethylene phthalides, m.p. (EtOH) unclear. (Found; C, 71.40; H, 4.09; N, 7.42; $C_{11}H_7NO_2$ requires; C, 71.35; H, 3.81; N, 7.56%).

b. 2-Cyano-4-methyl indan-1,3-dione

The mixture phthalides prepared in Example 4 (a) (2.1 g) were refluxed with a solution of sodium (0.25 g) in methanol (11 ml) for 20 mins. and worked up as described to give the title compound as a yellow solid; m.p. (water, hydrochloric acid) 188°–190° C (d). (Found; C, 70.77; H, 4.14; N, 7.18; $C_{11}H_7NO_2$ requires; C, 71.35; H, 3.81; N, 7.56%).

EXAMPLE 5

2-Cyano-4-methoxy indan-1,3-dione

A mixture of dimethyl 3-methoxy phthalate (18.1 g; 0.0845 mole), acetonitrile (8.7 g; 0.212 mole) and sodium methoxide (9.1 g; 0.17 mole) were stirred at 100° C for 6 hours, a further 10 ml of the nitrile being added after one hour. After cooling and dilution with dry ether the precipitated yellow solid was filtered off, dissolved in a minimum of water and reprecipitated with hydrochloric acid as an orange-yellow solid, m.p. 186°–189° C (d). (Found; C, 60.22; H, 4.10; N, 6.15; $C_{11}H_7NO_3.H_2O$ requires; C, 60.28; H, 4.14; N, 6.39%.)

EXAMPLE 6

5,6-Benzo-2-cyano indan-1,3-dione

Using the procedure outlined in Example 5, dimethyl naphthalene-2,3-dicarboxylate (24.4 g; 0.1 mole) was converted into the title compound, m.p. (water, hydrochloric acid) 264°–265° C (d). (Found; C, 70.02; H, 3.93; H, 5.60; $C_{14}H_7NO_2.H_2O$ requires; C, 70.29; H, 3.79; N, 5.85%.)

EXAMPLE 7

5-Chloro-2-cyano indan-1,3-dione

Dimethyl 4-chloro phthalate (28.3 g; 0.13 mole) was condensed with acetonitrile (13.0 g; 0.345 mole) in the presense of sodium methoxide (13.75 g; 0.25 mole) as described in Example 5 to yield the 2-cyano indandione, m.p. (benzene) 162°–170° C (d). (Found; C, 58.49; H, 1.98; N, 6.79; Cl, 16.79; $C_{10}H_4ClNO_2$ requires; C, 58.41; H, 1.96; N, 6.81; Cl, 17.25%.)

EXAMPLE 8 a. 6,7-Diethyl-1-tetralone 3-(3',4'-Diethylbenzoyl) propionic acid (m.p. 93° C), prepared by the acylation of 1,2-diethylbenzene with succinic anhydride, was catalytically reduced to 4-(3'4'-diethylphenyl) butanoic acid (b.p. 0.7 143°–147° C). A mixture of this acid (59 g; 0.27 mole) and 85% polyphosphoric acid (450 g) was warmed to 80° C stirring for 30 mins., cooled and poured onto 1 liter of ice-water. The oily product was extracted into ether, washed with water, saturated sodium bicarbonate solution, water and dried over $MgSO_4$.

Evaporation gave an oil which gave on distillation 48.30 g (89%) of tetralone b.p. 0.7. 118°–122° C.

(Found; C, 82.95; H, 9.21; $C_{14}H_{18}O$ requires; C, 83.12; H, 8.97%).

Alternatively 4-(3',4'-diethylphenyl) butanoic acid (23.3 g; 0.106 mole) may be cyclised by stirring at 100° C with 80% sulphuric acid (115 ml) for 1½ hours. After dilution, extraction into ether, and distillation 15.83 g (74%) of the tetralone was obtained.

b. 6,7-Diethyl-2-hydroxy-1,4-naphthoquinone

A 1M solution of potassium t-butoxide in dry t-butanol (2 liters) was saturated with oxygen and 6,7-diethyl-1-tetralone (48 g; 0.24 mole) was added. The mixture was stirred at ambient temperature until 2 equivalents of oxygen were absorbed when the red solution was cooled and acidified with concentrated hydrochloric acid. After removal of most of the t-butanol in vacuo the residue was partitioned between water and chloroform and the organic phase extracted with saturated sodium bicarbonate solution. Acidification of the bicarbonate extracts afforded 34.60 g (63%) of the naphthoquinone as an orange-yellow solid. Recrystallisation from aqueous ethanol in the presence of charcoal gave a yellow crystalline product of m.p. 105°–109° C. (Found; C, 70.45; H, 6.10; $C_{14}H_{14}O_3.½H_2O$ requires; C, 70.28; H, 6.32%).

c. 2-Chloro-6,7-diethyl-1,4-naphthoquinone

A solution of 6,7-diethyl-2-hydroxy-1,4-naphthoquinone (22 g; 0.096 mole) in thionyl chloride (250 ml) was refluxed for 12 hours and the solvent removed in vacuo. Repeated evaporation with dry benzene gave an orange solid which after recrystallisation from ethanol in the presence of charcoal weighed 18.04 g (76%) and had m.p. 90°–92° C. (Found; C, 67.21; H, 5.39; Cl, 14.21; $C_{14}H_{13}ClO_2$ requires; C, 67.61; H, 5.27; Cl, 14.26%).

d. 2-Azido-6,7-diethyl-1,4-naphthoquinone

An aqueous solution of sodium azide (6.15 g; 0.095 mole) was added in one portion to a stirred, refluxing solution of 2-chloro-6,7-diethyl-1,4-naphthoquinone (18.0 g; 0.073 mole) in ethanol (180 ml) and the mixture refluxed for a further 2 mins. The red solution was cooled and the orange solid filtered off and washed with cold ethanol then water. After drying the product weighed 13.87 g (75%) and had m.p. 73°–76° C (d). Recrystallisation from ethanol gave long orange needles of m.p. 74°–76° C (d). (Found; C, 65.64; H, 5.27; N, 16.66; $C_{14}H_{13}N_3O_2$ requires; C, 65.87; H, 5.13; N, 16.46%).

e. 3-Cyanomethylene-5,6-diethylphthalide

2-Azido-6,7-diethyl-1,4-naphthoquinone (6.0 g; 0.024 mole) was added portionwise to cold (0°–5° C), stirred concentrated sulphuric acid (100 ml) over 2 hours and the red solution stirred at this temperature till no further nitrogen evolution was noticed (ca. 15 mins.). The products from two such reactions carried out simultaneously were poured into 1200 ml of ice-water and the lilac solid filtered off and washed well with water. Recrystallisation from ethanol in the presence of charcoal give the title compound 5.00 g (47%) as an off-white solid of m.p. 147°–158° C. Further recrystallisation gave a white sample of m.p. 159°–168° C. shown by nmr to be a mixture of E and Z isomers. (Found; C, 73.70; H, 5.95; N, 5.94; $C_{14}H_{13}NO_2$ requires; C, 73.99; H, 5.77; N, 6.16%).

f. 2-Cyano-5,6-diethyl indan-1,3-dione

A mixture of 3-cyanomethylene-5,6-diethylphthalide (4.7 g; 0.021 mole) and methanolic sodium methoxide (from sodium [0.48 g] and methanol [21 ml]) was refluxed for 20 mins., cooled, and the red solution poured into 5N hydrochloric acid (100 ml). The precipitated yellow solid was filtered off and dried in vacuo over $P_2O_5$/NaOH to yield 3.711 g (79%) of material of m.p. 172°–173° C (d). (Found; C, 73.60; H, 5.94; N, 6.13; $C_{14}H_{13}NO_2$ requires; C, 73.99; H, 5.77; N, 6.16%).

EXAMPLE 9

3-Cyano-4-hydroxycoumarin

2-Acetoxybenzoyl chloride (13.45 g) in dry ether (100 ml) was added slowly to a stirred, refluxing suspension of the sodium salt of ethyl cyanoacetate [from ethyl cyanoacetate (21.98 g) and a 60% suspension of sodium hydride in mineral oil (7.82 g)] in dry ether (300 ml). Refluxing was continued for 18 hours, the mixture cooled and poured into water (700 ml) containing 10N sodium hydroxide (20 ml). The alkaline phase was separated, washed with ether (× 1), acidified with cold 12N hydrochloric acid and filtered. Recrystallisation form water-hydrochloric acid, using decolourising charcoal, gave 3-cyano-4-hydroxycoumarin, m.p. 267°–269° (d). (Found; C, 64.28; H, 2.90; N, 7.07. $C_{10}H_5NO_3$ requires C, 64.18; H, 2.69; N, 7.48).

EXAMPLE 10

3-Cyano-6-ethyl-4-hydroxy-7-methyl coumarin a. 5-Ethyl-4-methylsalicylic acid

A mixture of 4-ethyl-3-methylphenol (31.51 g) and anhydrous potassium carbonate (91.25 g) was heated at 175° for 4 hours under a carbon dioxide pressure of 1,300 p.s.i. The cooled reaction products were dissolved in water (2 l). Acidification with hydrochloric acid, filtration and recrystallisation of the solid from ethanol-water gave 5-ethyl-4-methylsalicylic acid, m.p. 152.5°–154° C. (Found; C, 66.55; H, 6.71; $C_{10}H_{12}O_3$ requires; C, 66.65; H, 6.71.)

b. 2-Acetoxy-5-ethyl-4-methylbenzoic acid

A mixture of 5-ethyl-4-methylsalicylic acid (15.00 g), acetic anhydride (80 ml) and acetic acid (80 ml) was heated under reflux for 1.5 hours, poured into water (1 l) and allowed to stand overnight. The solid formed was filtered off and recrystallised from benzene to give 2-acetoxy-5-ethyl-4-methylbenzoic acid, m.p. 132°–134° C. (Found; C, 64.71; H, 6.46; $C_{12}H_{14}O_4$ requires; C, 64.85; H, 6.35).

c. 2-Acetoxy-5-ethyl-4-methylbenzoyl chloride

A mixture of 2-acetoxy-5-ethyl-4-methylbenzoic acid (11.10 g) and thionyl chloride (20 ml) in dry benzene (100 ml) was heated under reflux for 6 hours, cooled and solvents removed in vacuo. The crude 2-acetoxy-5-ethyl-4-methylbenzoyl chloride was obtained as a liquid which was used as rapidly as possible in the next stage of the synthesis without further purification.

d. 3-Cyano-6-ethyl-4-hydroxy-7-methyl coumarin

2-Acetoxy-5-ethyl-4-methylbenzoyl chloride (11.5 g) in dry ether (75 ml) was added slowly to a stirred, refluxing suspension of the sodium salt of ethyl cyanoacetate [prepared from ethyl cyanoacetate (14.97 g) and a 60% suspension of sodium hydride in mineral oil (5.00 g)] in dry ether (275 ml). Refluxing was continued for 18 hours, the mixture cooled and poured into water (500 ml) containing 2.5N sodium hydroxide (30 ml). The alkaline phase was separated, washed with ether (× 3), acidified with 12N hydrochloric acid and filtered. Recrystallisation from ethanol-dilute hydrochloric acid gave 3-cyano-6-ethyl-4-hydroxy-7-methyl coumarin, m.p. 224°–226° C. (Found; C, 68.22; H, 5.01; N, 5.64; $C_{13}H_{11}NO_3$ requires; C, 68.11; H, 4.84; N, 6.11.)

EXAMPLE 11

3-Cyano-6,7-dimethyl-4-hydroxycoumarin monohydrate

3-Cyano-6,7-dimethyl-4-hydroxy coumarin monohydrate, m.p. (EtOH - dil. HCl) 262°–264° C. (Found; C, 62.09; H, 4.83; N, 5.62; $C_{12}H_9NO_3$. $1H_2O$ requires; C, 61.80; H, 4.75; N, 6.01) was prepared from 3,4-dimethylphenol via 4,5-dimethylsalicylic acid (m.p. 204°–205°), 2-acetoxy-4,5-dimethylbenzoic acid (m.p. 128°–130°) and 2-acetoxy-4,5-dimethylbenzoyl chloride by an analogous procedure to that described in Example 10.

EXAMPLE 12

3-Cyano-6,7-diethyl-4-hydroxy coumarin

3-Cyano-6,7-diethyl-4-hydroxy coumarin, m.p. (EtOH - dil. HCl then $CHCl_3$ - pet. ether) 198°–200°. (Found; C, 68.76; H, 5.33; N, 5.68; $C_{14}H_{13}NO_3$ requires; C, 69.12; H, 5.39; N, 5.76) was prepared from 3,4-diethylphenol via 4,5-diethylsalicylic acid (m.p. 126°–128.5°), 2-acetoxy-4,5-diethylbenzoic acid (m.p. 127°–9°) and 2-acetoxy-4,5-diethylbenzoyl chloride by an analogous procedure to that described in Example 10.

EXAMPLE 13

3-Cyano-4-hydroxy-6-methyl coumarin

3-Cyano-4-hydroxy-6-methyl coumarin, m.p. (EtOH - dil. HCl) 238°–241°, (Found; C, 65.32; H, 3.80; N, 6.98; $C_{11}H_7NO_3$ requires C, 65.57; H, 3.51; N, 6.96) was prepared from 4-methylphenol via 5-methylsalicylic acid (m.p. 147°–149°), 2-acetoxy-5-methylbenzoic acid (m.p. 142°–144°) and 2-acetoxy-5-methylbenxoyl chloride by an analogous procedure to that described in Example 10.

EXAMPLE 14

3-Cyano-4-hydroxy-7-methyl coumarin

3-Cyano-4-hydroxy-7-methyl coumarin, m.p. (EtOH - dil. HCl) 261°–264°, (Found; C, 65.15; H, 3.86; N, 6.39; $C_{11}H_7NO_3$ requires C, 65.67; H, 3.51; N, 6.96) was prepared from 4-methylsalicylic acid via 2-acetoxy-4-methyl-benzoic= acid (m.p. 132°–133°) and 2-acetoxy-4-methylbenxoyl chloride (b.p. 120°–122°/1.5 mm) by an analogous procedure to that described in Example 10.

EXAMPLE 15

3-Cyano-7-ethyl-4-hydroxy coumarin

3-Cyano-7-ethyl-4-hydroxy coumarin, m.p. (EtOH - dil. HCl) 211°–215°. (Found; C, 66.60; H, 4.55; N, 6.05; $C_{12}H_9NO_3$ requires C, 66.97; H, 4.22; N, 6.51) was prepared from 3-ethylphenol via 4-ethylsalicylic acid (m.p. 122.5°–125.5°), 2-acetoxy-4-ethylbenzoic acid (m.p. 84°–87°) and 2-acetoxy-4-ethylbenxoyl chloride by an analogous procedure to that described in Example 10.

EXAMPLE 16

3-Cyano-7-ethyloxy-4-hydroxy coumarin monohydrate

3-Cyano-7-ethyloxy-4-hydroxy coumarin monohydrate, m.p. (EtOH - dil. HCl) 224°–225°, (Found; C, 57.97; H, 4.50; N, 5.44; $C_{12}H_9NO_4.H_2O$ requires C, 57.83; H, 4.45; N, 5.62) was prepared from 4-ethyloxysalicylic acid via 2-acetoxy-4-ethyloxybenzoic acid (m.p. 122°–124°) and 2-acetoxy-4-ethyloxybenzoyl chloride by an analogous procedure described in Example 10.

EXAMPLE 17

3-Cyano-4-hydroxy-2-oxo-2H-naphtho[2,3-b] pyran

3-Cyano-4-hydroxy-2-oxo-2H-naphtho [2,3-b] pyran, m.p. (EtOH - dil. HCl) 297°–299°, (Found; C, 70.50; H, 3.17; N, 5.60; $C_{14}H_7NO_3$ requires C, 70.89; H, 2.97; N, 5.90) was prepared from 3-hydroxy-2-naphthaic acid via 3-acetoxy-2-naphthoic acid (m.p. 182°–185°) and 3-acetoxy-2-naphthoyl chloride (m.p. 88°–89°) by an analogous procedure to that described in Example 10.

EXAMPLE 18

3-Cyano-4-hydroxy-2-oxo-6,7,8,9-tetrahydro-2H-naphtho [2,3-b] pyran

3-Cyano-4-hydroxy-2-oxo-6,7,8,9-tetrahydro-2H-naphtho [2,3-b] pyran, m.p. (EtOH - dil. HCl) 265°–267°, (Found; C, 69.44; H, 4.90; N, 5.39; $C_{14}H_{11}NO_3$ requires C, 69.70; H, 4.60; N, 5.81) was prepared from 5,6,7,8-tetrahydro-2-naphthol via 3-hydroxy-5,6,7,8-tetrahydro-2-naphthoic acid (m.p. 180°–182°), 3-acetoxy-5,6,7,8-tetrahydro-2-naphthoic acid (m.p. 149°–150°) and 3-acetoxy-5,6,7,8-tetrahydro-2-naphthoyl chloride by an analogous procedure to that described in Example 10.

EXAMPLE 19

3-Cyano-4-hydroxy-8-methylcoumarin monohydrate

3-Cyano-4-hydroxy-8-methylcoumarin monohydrate, m.p. (aq. EtOH - dil. HCl) 211°–4° (Found; C, 60.04; H, 4.26; N, 5.91. $C_{11}H_7NO_3.H_2O$ requires C, 60.28; H, 4.14; N, 6.39) was prepared from 3-methylsalicylic acid via 2-acetoxy-3-methylbenzoic acid (m.p. 115°–7°) and 2-acetoxy-3-methylbenzoyl chloride by an analogous procedure to that described in Example 10.

EXAMPLE 20

3-Cyano-4-hydroxy-6-methyloxycoumarin

3-Cyano-4-hydroxy-6-methyloxycoumarin, m.p. ($H_2O$ - dil. HCl) 249°–253° (d), (Found; C, 59.67; H, 3.22; N, 6.41. $C_{11}H_7NO_4$ requires C, 60.83; H, 3.25; N, 6.45) was prepared from 5-methyloxysalicylic acid via 2-acetoxy-5-methyloxybenzoic acid (m.p. 156°–8°) and 2-acetoxy-5-methyloxybenzoyl chloride by an analogous procedure to that described in Example 10.

EXAMPLE 21

3-Cyano-7,8-dimethyl-3-hydroxycoumarin monohydrate

3-Cyano-7,8-dimethyl-4-hydroxycoumarin monohydrate, m.p. (EtOH - pet. ether) 255°–6°, (Found; C, 62.04; H, 4.80; N, 6.04. $C_{12}H_9NO_3.H_2O$ requires C, 61.79; H, 4.76; N, 6.01) was prepared from 2,3-dimethylphenol via 3,4-dimethylsalicylic acid (m.p. 192°–3°), 2-acetoxy-3,4-dimethylbenzoic acid (m.p. 142°–4°) and 2-acetoxy-3,4-dimethylbenzoyl chloride by an analogous procedure to that described in Example 10.

BIOLOGICAL DATA

The compounds prepared in the preceding examples were tested in the rat Passive Cutaneous Anaphylaxis Test (PCA test), described below. They were administered as their sodium salts either in pH 7.2 phosphate buffer (for soluble salts) or as a suspension in 1% methyl cellulose (for insoluble salts).

i. Serum containing heat labile homocytotropic antibody was raised in rats by a method similar to that used by Mota. (I. Mota Immunology 1964, 7, 681).

Male Wistar rats of 250–300 g, were injected intraperitoneally with 0.5 ml. of Bordatella pertussis vaccine (containing $4 \times 10^{10}$ dead organism per ml) and subcutaneously with 0.5 ml. of an emulsion of 100 mg. of ovalbumin in 2 ml. of saline and 3 ml. of incomplete Freunds' adjuvant. Rats were bled by cardiac puncture on day 18, the blood was pooled and separated and serum stored at −20° and thawed only once before use.

ii. The P.C.A. test was similar to that described by Ovary and Bier (A. Ovary and O. E. Bier, Prod. Soc. Exp. Biol. Med. 1952, 81, 584) and Goose and Blair (J. Goose and A. M. J. N. Blair, Immunology 1969, 16, 769).

0.1 ml. of each of six twofold serial dilutions of the serum in 0.9% saline were injected intradermally into separate sites on the shaved dorsal surface of 250–350 g. Male Wistar rats. 72 hours later the animals were challenged by i.v. injection of 0.3 ml. of 1% ovalbumin mixed with 0.1 ml. of a 5% solution of pontamine sky blue dye both in isotonic saline buffered with pH 7.2 Sorenson buffer (P.B.S.). The rats were killed after 20 minutes and the diameter of the blue wheals at the antibody injection sites were measured. The starting dilution of the serum was adjusted so that there was no response, after challenge, at the site of injection of the highest dilution and a maximum response at the two or three lowest dilutions. Typically, six twofold serial dilutions of the serum ¼ to 1/128 were used.

Compounds were tested for their ability to reduce the diameter of the wheals at the injection sites of dilutions of antibody which on all the controls have less than maximum response. Amounts of the compounds were administered to rats by subcutaneous injection, into the nucal region, of a solution of the compound in P.B.S. or as a suspension in 1% methyl cellulose, each amount a test group of six animals at a specified time prior to intravenous challenge with ovalbumin. The diameters of the blue wheals which developed on the test group of animals were compared with those on a control group of six animals treated in the same way as the test group, but which had received an equivalent subcutaneous injection of the carrier fluid of the same volume but not containing the compound under test.

% Inhibition of P.C.A. = 100 (1 - a/b)

$a$ = The mean of the sum of the diameters of the wheals produced in the test group of animals at those antibody sites where all the control group of animals gave less than maximum response.

$b$ = The mean of the sum of diameters of the wheals produced in the control group of animals at those antibody sites where all the animals in group gave less than maximum response.

The preferred method of administration was a solution of the test compound dissolved in pH 7.2 buffer and neutralised with sodium bicarbonate. For those compounds having insoluble sodium salts, the salts were isolated by reaction of the free cyano compound with 2.5N sodium hydroxide and the filtered sodium salt washed free of alkali with water. The dried salts were then administered as a suspension in 1% methyl cellulose.

| BIOLOGICAL RESULTS | | | |
|---|---|---|---|
| | Dose (mg/kg) | Time (mins.) | % Inhibition of PCA response |
| Example 1 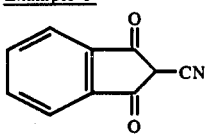 | 25 | 0 | 43 |
| | 100 | 0 | 64 |
| | 25 | 30 | 8 |
| | 100 | 30 | 16 |
| Example 2 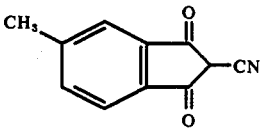 | 25 | 0 | 45 |
| | 100 | 0 | 76 |
| | 25 | 30 | 15 |
| | 100 | 30 | 35 |
| Example 3 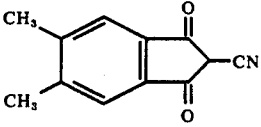 | 2.5 | 10 | 46 |
| | 5 | 10 | 56 |
| | 10 | 10 | 77 |
| | 20 | 10 | 92 |
| Example 4 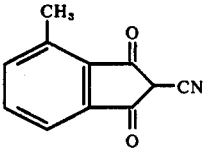 | 5 | 10 | 21 |
| | 10 | 10 | 25 |
| | 20 | 10 | 75 |
| | 40 | 10 | 83 |
| Example 5 | | | |

-continued

BIOLOGICAL RESULTS

| Structure | Dose (mg/kg) | Time (mins.) | % Inhibition of PCA response |
|---|---|---|---|
| 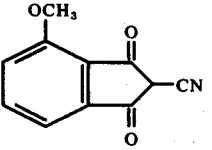 Example 6 | 5<br>10<br>20<br>40 | 10<br>10<br>10<br>10 | 28<br>16<br>57<br>81 |
| 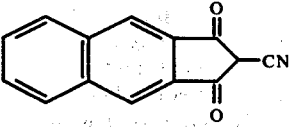 Example 7 | 25<br>100<br>25<br>100 | 10<br>10<br>30<br>30 | 88<br>70<br>27<br>30 |
| 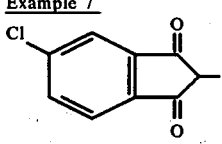 Example 8 | 10<br>25<br>10<br>25 | 10<br>10<br>30<br>30 | 33<br>76<br>21<br>15 |
| 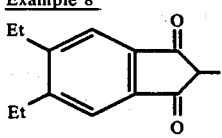 Example 9 | 5<br>10<br>20<br>40 | 10<br>10<br>10<br>10 | 74<br>90<br>78<br>64 |
| 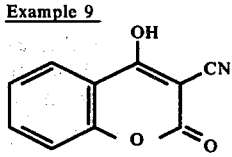 Example 10 | 25<br>100<br>25<br>100 | 0<br>0<br>30<br>30 | 64<br>87<br>30<br>40 |
| 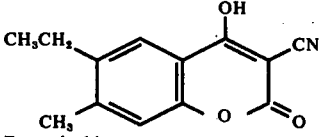 Example 11 | 10<br>25<br>10<br>25 | 10<br>10<br>30<br>30 | 71<br>67<br>24<br>17 |
| 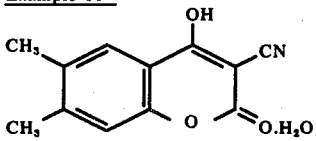 Example 12 | 25<br>100<br>25<br>100 | 0<br>0<br>30<br>30 | 51<br>72<br>16<br>11 |
| 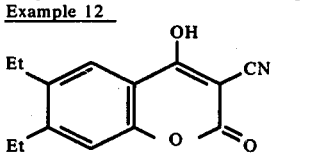 Example 13 | 2.5<br>5<br>10<br>20 | 10<br>10<br>10<br>10 | 64<br>72<br>68<br>93 |
| 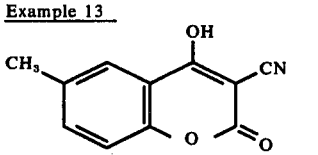 Example 14 | 25<br>100<br>25<br>100 | 0<br>0<br>30<br>30 | 14<br>40<br>21<br>22 |
| 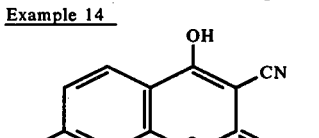 Example 15 | 25<br>100<br>25<br>100 | 0<br>0<br>30<br>30 | 45<br>74<br>14<br>18 |
| 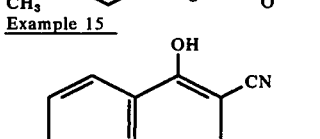 Example 16 | 25<br>100<br>25<br>100 | 0<br>0<br>30<br>30 | 34<br>64<br>27<br>17 |

BIOLOGICAL RESULTS -continued

| Structure | Dose (mg/kg) | Time (mins.) | % Inhibition of PCA response |
|---|---|---|---|
| Example 17 | 5 | 10 | 59 |
| | 10 | 10 | 71 |
| | 20 | 10 | 86 |
| | 40 | 10 | 73 |
| Example 18 | 25 | 0 | 9 |
| | 100 | 0 | 15 |
| | 25 | 60 | 23 |
| | 100 | 60 | 18 |
| Example 19 | 1 | 10 | 2 |
| | 2 | 10 | 22 |
| | 4 | 10 | 52 |
| | 8 | 10 | 67 |
| Example 20 | 25 | 0 | 48 |
| | 100 | 0 | 67 |
| | 25 | 30 | 23 |
| | 100 | 30 | 35 |
| Example 21 | 25 | 0 | 54 |
| | 100 | 0 | 72 |
| | 25 | 30 | 29 |
| | 100 | 30 | 36 |
| | 2.5 | 10 | 20 |
| | 5 | 10 | 39 |
| | 10 | 10 | 65 |
| | 20 | 10 | 97 |

We claim:

1. A compound of the formula

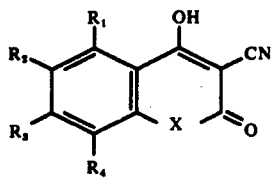

or a pharmaceutically acceptable, nontoxic salt thereof or hydrate thereof, wherein $R_1$, $R_2$, $R_3$ and $R_4$ are each hydrogen, halogen, alkyl of 1 to 6 carbon atoms or alkoxy of 1 to 6 carbon atoms or any adjacent two of the groups $R_1$, $R_2$, $R_3$, $R_4$ taken together with the carbon atoms to which they are joined complete a carbocyclic ring unsubstituted or substituted by one or more members selected from the group consisting of halogen, alkyl of 1 to 6 carbon atoms or alkoxy of 1 to 6 carbon atoms, and X is an oxygen atom, provided that the groups $R_1$, $R_2$, $R_3$ and $R_4$ are not all simultaneously hydrogen atoms.

2. A compound according to claim 1 wherein $R_1$ and $R_4$ are each hydrogen and one or both of the groups $R_2$ and $R_3$ are methyl, ethyl, n-propyl, methoxy, ethoxy or n-propoxy.

3. The compound according to claim 1 which is 3-cyano-6-ethyl-4-hydroxy-7-methyl coumarin.

4. The compound according to claim 1 which is 3-cyano-6,7-dimethyl-4-hydroxy coumarin monhydrate.

5. The compound according to claim 1 which is 3-cyano-6,7-diethyl-4-hydroxy coumarin.

6. The compound according to claim 1 which is 3-cyano-4-hydroxy-6-methyl coumarin.

7. The compound according to claim 1 which is 3-cyano-4-hydroxy-7-methyl coumarin.

8. The compound according to claim 1 which is 3-cyano-7-ethyl-4-hydroxy coumarin.

9. The compound according to claim 11 which is 3-cyano-7-ethoxy-4-hydroxy coumarin monohydrate.

10. The compound according to claim 1 which is 3-cyano-4-hydroxy-2-oxo-2H-naphtho[2,3-b]pyran.

11. The compound according to claim 1 which is 3-cyano-4-hydroxy-2-oxo-6,7,8,9-tetrahydro-2H-naphtho[2,3-b]pyran.

12. The compound according to claim 1 which is 3-cyano-4-hydroxy-8-methyl coumarin monohydrate.

13. The compound according to claim 1 which is 3-cyano-4-hydroxy-6-methoxy coumarin.

14. The compound according to claim 1 which is 3-cyano-7,8-dimethyl-4-hydroxy coumarin monohydrate.

15. A compound according to claim 1 in the form of its sodium or potassium salt.

16. A compound according to claim 1 wherein $R_1$, $R_2$, $R_3$ and $R_4$ are each hydrogen, halogen, alkyl of 1 to 3 carbon atoms or alkoxy of 1 to 3 carbon atoms, or any adjacent two of the groups $R_1$, $R_2$, $R_3$ and $R_4$, taken together with the carbon atoms to which they are joined, form a fused phenyl, 1,2-cyclopentylene or 1,2-cyclohexenylene ring.

17. A compound according to claim 1 in the form of a pharmaceutically acceptable, nontoxic salt wherein the salt is an alkali metal salt, an alkaline earth metal salt, an amine salt or an amino salt.

* * * * *